US005110805A

United States Patent [19]

Berner et al.

[11] Patent Number: 5,110,805

[45] Date of Patent: May 5, 1992

[54] METHOD FOR PROTECTING PLANTS AGAINST SOIL-BORNE FUNGI USING GLYPHOSATE AND IMAZAQUIN COMPOSITIONS

[75] Inventors: Dana K. Berner; Gerard T. Berggren; Johnnie P. Snow, all of Baton Rouge, La.

[73] Assignee: The Board of Supervisors of Louisiana State University, Baton Rouge, La.

[21] Appl. No.: 590,478

[22] Filed: Sep. 28, 1990

[51] Int. Cl.$^5$ .............................................. A01N 57/20

[52] U.S. Cl. ........................................ 514/76; 514/75; 514/314; 71/86; 71/92

[58] Field of Search ....................... 514/76, 314; 71/86, 71/92

[56] References Cited

U.S. PATENT DOCUMENTS 3,799,758 3/1974 Franz ..................................... 71/86
4,798,619 1/1989 Los ......................................... 71/92

OTHER PUBLICATIONS

Chemical Abstracts 102:42757g Abstracting: Bode et al., "Mode of Action of Glyphosate in Candida maltosa", Archives of Microbiology, vol. 140 (1), 1984, pp. 83–85.

Chemical Abstracts 113: 54241z (Aug. 13, 1990) Abstracting: Moseley et al., "Reducing Herbicide Inputs When Establishing No-Till Soybeans", Weed Technology, vol. 4(1), 1990, pp. 14–19.

The Agrochemicals Handbook, 2nd Edition–Nottingham, England, The Royal Society of Chemistry, 1987, P.A.927.

*Primary Examiner*—Allen J. Robinson
*Assistant Examiner*—John D. Pak
*Attorney, Agent, or Firm*—Robert C. Tucker; William David Kiesel

[57] ABSTRACT

A method for protecting crops against soil-borne fungi, which method comprises: treating the soil with a fungicidal effective amount of a composition selected from: (a) an N-phosphonomethyl glycine, or salt thereof; (b) a 2-(2-imidazolin-2 yl)quinoline, or salt thereof; and (c) mixtures thereof.

3 Claims, 3 Drawing Sheets

METHOD FOR PROTECTING PLANTS AGAINST SOIL-BORNE FUNGI USING GLYPHOSATE AND IMAZAQUIN COMPOSITIONS

FIELD OF THE INVENTION

The present invention relates to a method for protecting crops against soil-borne fungi, which method comprises: treating the soil with a fungicidal effective amount of a composition selected from: (a) an N-phosphonomethyl glycine, or salt thereof; (b) a 2-(2-(2-imidazolin-2yl)quinoline, or salt thereof; and (c) mixtures thereof.

BACKGROUND AND SUMMARY OF THE INVENTION

Substantial amounts of crops are lost each year to fungal diseases caused by soil-borne fungi. Present control measures include the use of resistant varieties of crops and practices directed toward avoiding or reducing initial inoculum, such as delayed planting, and in the case of peanuts, soil fumigation. Fumigation is expensive and conventional fungicides have heretofore not been identified that can economically control such fungus caused diseases as red crown rot. Consequently, there is a great need for ever impoved fungicidal formulations to mitigate these problems. It has unexpectedly been discovered, by the inventors hereof, that two classes of compounds, both of which are known herbicides, exhibit fungicidal properties, particularly against Calonectria crotalariae, a soil-borne fungus that attacks soybean, peanut, papaya, blueberry, as well as other plant species.

The fungicidal compositions of the present invention are selected from: (a) a compound selected from the N-phosphonomethyl glycines, and salts thereof, sometimes herein referred to as the glyphosate derivatives; (b) a compound selected from the 2-(2-imidazolin-2yl)-quinolines, and salts thereof, sometimes herein referred to as the quinoline derivatives; and (c) mixtures thereof.

In a preferred embodiment of the present invention, compound (a) is the isopropylamine salt of N-phosphonomethyl glycine, and compound (b) is 2-[4,5-dihydro-4-methyl-4-(1-methylethyl)-5-oxo-1H-imidazol-2yl]-3-quinoline carboxylic acid.

DETAILED DESCRIPTION OF THE INVENTION

Figure 1:
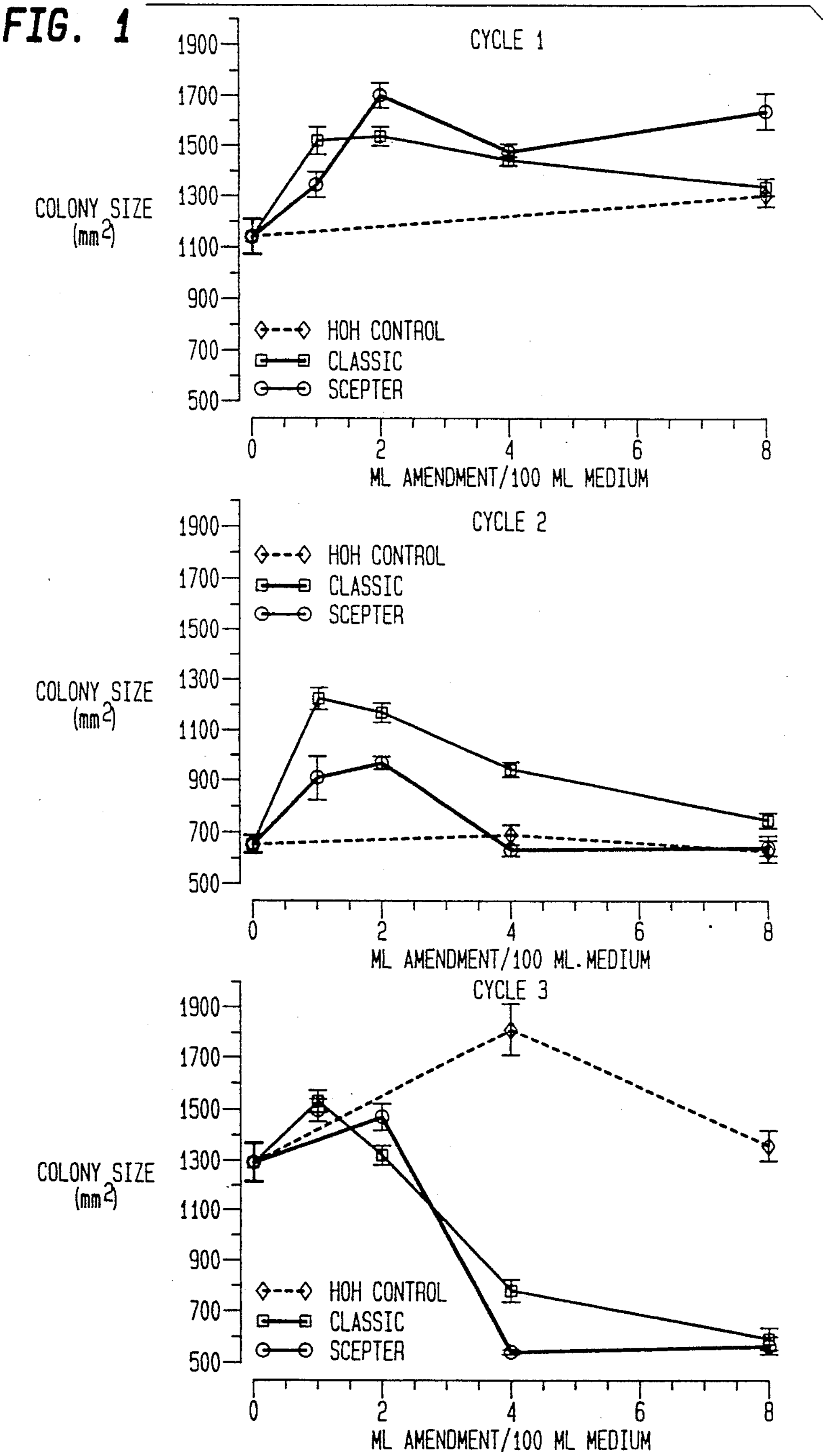
FIG. 1 is a plot of Calonectria crotalariae colony size versus application rates for 2-[4,5-dihydro-4-methyl-4-(1-methylethyl)-5-oxo-1H-imidazol-2yl ]-3-quinoline carboxylic acid and chlorimuron ethyl for three cycles of treatment.

Soil-borne fungi cause a variety of diseases on crops. For example, Calonectria crotalariae, a soil-borne fungal pathogen, causes Cylindrocladium black rot on peanuts, red crown rot on soybeans, and other diseases on plants such as blueberry and papaya. The fungus overwinters in the soil and crop debris as small microsclerotia which germinate in the spring and infect susceptible plant roots. General symptomology is expressed as dessication and necrosis of leaves resulting in the eventual death of severely infected plants. Yield losses for soybean and peanut crops can be as much as 50%. Chemical control measures are usually restricted to soil fumigation which is expensive and, depending on the crop, economically prohibitive.

The compositions used in the practice of the present invention represent an economical treatment against such fungal attack. As previously mentioned, the fungicical compositions of the present invention are known herbicides — not fungicides. What makes the present invention even more unexpected is the fact that one of the herbicides, the glyphosates, are non-selective post-emergence herbicides which control many annual and perennial grasses and broadleaf weeds, plus many tree and woody brush species in cropland and noncrop sites. The other known herbicide, the quinoline derivatives, also sometimes referred to as the imazaquin derivatives, may be applied preplant, preemergence or postemergence, especially with soybeans.

The N-phosphonomethyl glycines are represented by the formula:

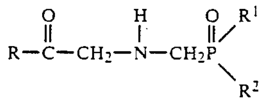

wherein R, $R^1$ and $R^2$ are independently selected from the group consisting of:

halogen; —OH; —SH;

—$NR^4R^5$ wherein $R^4$ and $R^5$ are independently selected from the group consisting of hydrogen, alkyl and hydroxyalkyl having 1 to 4 carbon atoms, alkenyl having 2 to 4 carbon atoms, and $R^4$ and $R^5$ taken together with the nitrogen atom can form a heterocyclic ring;

—$OR^3$ and —$SR^3$ wherein $R^3$ is selected from the group consisting of monovalent hydrocarbon groups, monovalent hydrocarbonoxyhydrocarbon groups, each containing from 1 to 18 carbon atoms, halogenated monovalent hydrocarbon groups, halogenated monovalent hydrocarbonoxyhydrocarbon groups groups each containing from 1 to 18 carbon atoms and from 1 to 3 halogens,

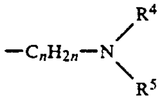

groups wherein n is from 1 to 4 and $R^4$ and $R^5$ are as defined above provided that no more than two of R, $R^1$ or $R^2$ can be —$NR^4R^5$, —$OR^3$ or —$SR^3$; and —$OR^6$ wherein $R^6$ is a salt-forming cation selected from the group consisting of cations of alkali metals, alkaline earth metals, copper, zinc, manganese, nickel, ammonium, organic ammonium, provided that when the organic group is aryl the ammonium salt is a primary amine salt, and mixtures of such salts, provided that when any one of R, $R^1$ or $R^2$ is halogen the others of R, $R^1$ or $R^2$ cannot be $-OR^6$, and further provided that no more than two of R, $R^1$, or $R^2$ are $-OR^6$ *when R6* is ammonium or organic ammonium; and —the strong acid salts of said compounds of the formula where R, $R^1$, and $R^2$ are —OH, said strong acid having a pK of 2.5 or less.

The organic ammonium salts of the above formula are those preferred from low molecular weight organic amines, i.e. those having a molecular weight below about 300. Such organic amines include the alkyl amines, alkylene amines and alkanol amines containing not more than 2 amine groups, such as the $C_1$–$C_{18}$ alkyl amines such as methylamine, ethylamine, n-propylamine, isopropylamine, n-butylamine, isobutylamine, sec-butylamine, n-amylamine, iso-amylamine, hexylamine, heptylamine, octylamine, nonylamine, decylamine, undecylamine, dodecylamine, tridecylamine, tetradecylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-amylamine, diisoamylamine, dihexylamine, di-heptylamine, dioctylamine, trimethylamine, triethylaimine, tri-n-propylamine, triisopropylamine, tri-n-butylamine, triisobutylamine, tri-secbutylamine, tri-n-amylamine, ethanolamine, n-propanolamine, isopropanolamine, diethanolamine, N,N-diethylethanolamine, N-ethylpropanolamine, N-butylethanolamine, allylamine, n-butenyl-2-amine, n-pentyl-2-amine, 2,3-dimethylbutenyl-2-amine, di-butenyl- 2-amine, n-hexenyl-2-amine and propylenediamine, primary aryl amines such as aniline, methoxyaniline, ethoxyaniline, o,m,p-toluidine, phenylenediamine, 2,4,6-tribromoaniline, benzidine, naphthylamine, o,m,p-chloroaniline, and the like; hetrocyclic amines such as pryidine, morpholine, piperidine, pyrrolidine, indoline, azepine and the like. Preferred are the $C_1$ to $C_{18}$ alkyl amines, more preferred are the $C_1$ to $C_{10}$ alkyl amines, and most preferred are the $C_1$ to $C_4$ alkyl amines, particularly isopylamine.

Among the preferred compounds of the present invention are those of the above formula wherein at least one of the R,$R^1$, and $R^2$ is $OR^3$ or $OR^6$ and the remaining members of R, $R^1$, and $R^2$ are OH, SH, or $OR^6$. The more preferred compounds of the present invention are those of the above formula wherein at least one of R, $R^1$, and $R^2$ is $OR^6$ and the remainder of R, $R^1$ and $R^2$ are OH, and wherein $R^6$ is a salt-forming cation. The particularly preferred compounds of this invention are those of the formula wherein one of R, $R^1$, and $R^2$ is $OR^6$, the remaining ones are OH, and $R^6$ is ammonium or organic ammonium wherein the organic ammonium group is defined as a group consisting of a positively charged nitrogen atom joined to from 1 to 4 aliphatic groups, each containing from 1 to 18 carbon atoms, preferably from 1 to 10 carbon atoms, and more preferably from 1 to 6 carbon atoms. Non limiting examples of such compounds include: monoalkylammonium, dialkylammonium, trialkylammonium, monoalkenylammonium, dialkenylammonium, trialkenylammonium, monoalkynylammonium, dialkynylammonium, trialkynyammonium, monoalkanolammonium, dialkanolammonium, trialkanolammonium, heterocyclic ammonium or an ary ammonium.

Most preferred are the readily water soluble compounds in which at least one of the hydrogens in the hydroxy or thiol groups of N-phosphonomethyl glycine has been replaced with an alkali metal or an alkaline earth metal or has been combined with ammonia or an organic amine, preferably a $C_1$ to $C_4$ alkylamine. The amino alkyl esters of N-phosphono-methyl glycine are also preferred.

The preparation of the above compounds is taught in U.S. Pat. Nos. 3,799,758 and 4,405,531 which are incorporated herein by reference.

The 2-(2-imidazolin-2-yl)quinoline compounds of the instant invention are those represented by the formula:

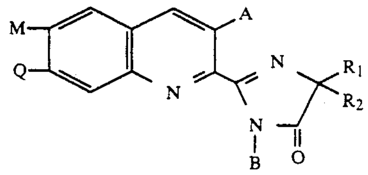

wherein $R_1$ is methyl, ethyl, isopropyl or cyclopropyl; A is $COOR_2$, $CH_2OH$ or CHO and $R_2$ is $C_1$–$C_8$ alkyl, hydrogen, $C_3$–$C_8$ alkenyl, $C_3$–$C_6$ cycloalkyl or a cation selected from the group consisting of alkali metals, alkaline earth metals, manganese, copper, iron, cobalt, lead, silver, nickel, ammonium, and organic ammonium; B is hydrogen or $COCH_3$; and M and Q each represent a member selected from hydrogen, halogen, methyl, methoxy, nitro, $CF_3$, CN, N(CH:), $NH_2$, $SCH_3$ or $SO_2CH_3$, provided that only one of M or Q may be a substituent other than hydrogen, halogen, methyl or methoxy.

A preferred group of 2-(2-imidazolin-2-yl)quinoline compounds represented by the above formula are those in which $R_1$ is isopropyl; M and Q are hydrogen, A is $COOR_2$ and $R_2$ is as defined above. The most preferred compound is when A is COOH and B, M and Q are each hydrogen, $R_2$ is isopropyl.

The preparation of the 2-(2-imidazolin-2-yl) quinoline compound is taught in U.S. Pat. No. 4,798,619, which is incorporated herein by reference.

Generally, the weight ratio of the glyphosate to quinoline component in the mixture of the present invention will be from about 0:100 to 100:0, preferably from about 20:80 to 80:20, and more preferably from about 60:40 to 40:60, and most preferably about 50:50.

Since the preferred group of compositions of the present I5 invention are salts which are water soluble, these compounds can simply be mixed and dispersed in water and applied as a dilute aqueous spray to the soil to be treated. The salts can also lend themselves to flowable concentrates. A typical flowable liquid can be prepared by admixing 40% by weight of active ingredient with about 2% by weight of a gelling agent such as bentonite, 3% by weight of a dispersing agent such as sodium lignosulfonate, 1% by weight of polyethylene glycol and 54% by weight of water.

It is also understood that the mixture of the present invention can also be applied as an emulsifiable concentrate. A typical emulsifiable concentrate can be prepared by dissolving about 5% to 25% by weight of the active components in about 65% to 90% by weight of N-methylpyrrolidone, isophorone, butyl cellosolve, methylacetate or the like and dispersing therein about 5% to 10% by weight of a nonionic surfactant such as an alklphenoxy polyethoxy alcohol. This concentrate is dispersed in water for application as a liquid spray.

The present invention will be illustrated in more detail with reference to the following examples, which should not be construed to be limiting in scope.

EXAMPLES

Three samples of the fungus Calonectria crotalariae were collected from soybean plants which exhibited red crown rot, from three different locations in Louisiana. Each of the three samples was isolated in Phipps' semi-selective media. In order to isolate Calonectria crotalariae from contamination of other fungi, the fungicide thiabendazole was used in the media because it is effective as a fungicide against soil-borne fungi except Calonectria crotalariae. Hyphal tips from each isolate were transferred to, and cultures maintained, on corn meal agar which was amended with 2 vol.% glycerol.

The culture media used in these examples was also Phipps'semi-selective media, but without thiabendazole. After liquifying, 100 ml aliquots of media were transferred to 250 ml Erlenmeyer flasks. The flasks were then autoclaved and allowed to cool to 45° C. before adding the amendments, or various concentrations, of test compositions. All of the test compositions used in these examples are commercially available herbicides. Prior to the present invention, none of them were known to exhibit significant fungicidal activity.

Figure 2:
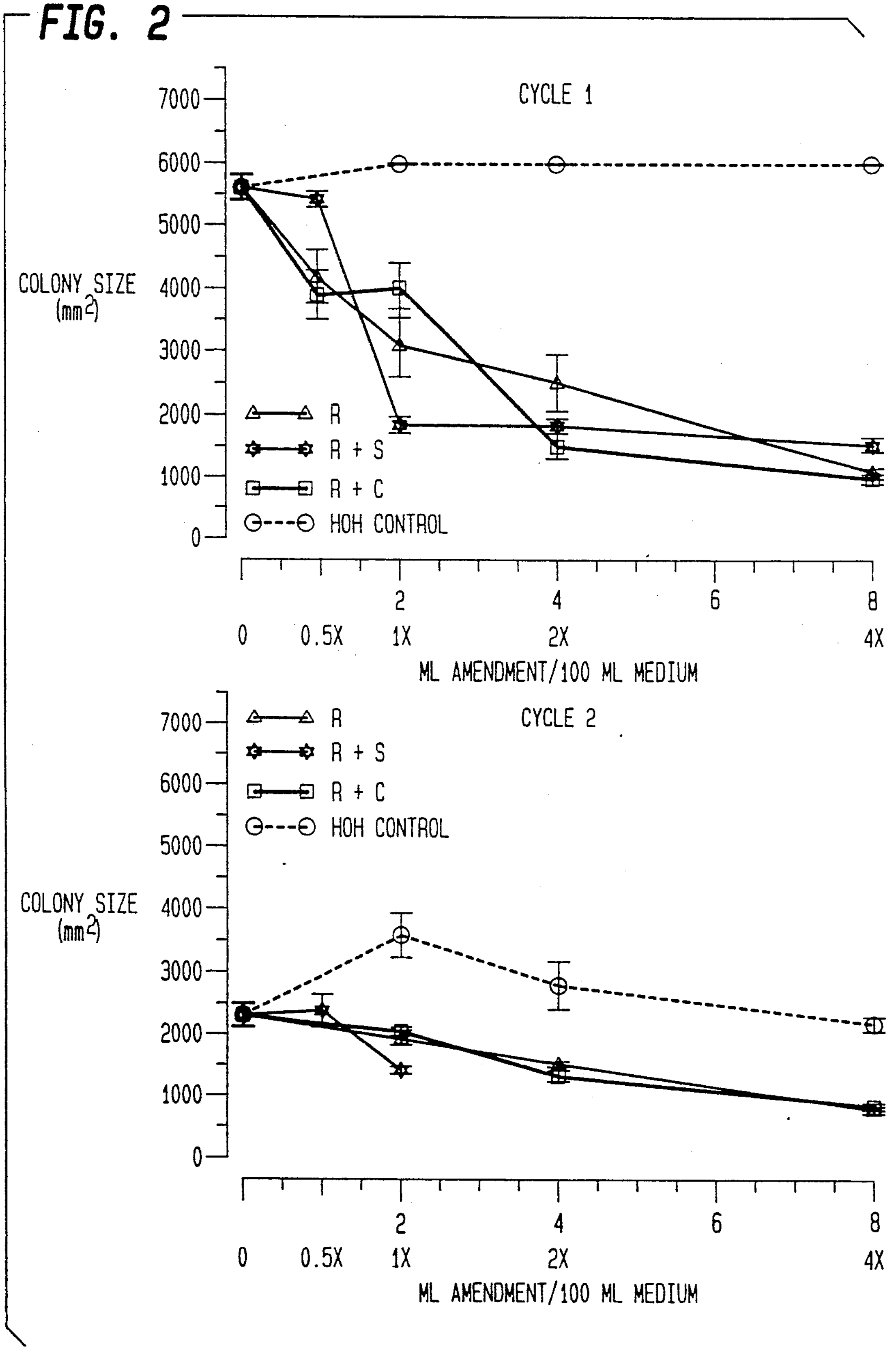
FIG. 2 is a plot of Calonectria crotalariae colony size versus application rate for the isopropylamine salt of N-phosphonomethyl glycine alone and in combination with 2-[4,5-dihydro-4-methyl-4-(1-methylethyl)-5-oxo-1H-imidazol-2yl]-3-quinoline carboxylic acid, and with chlorimuron ethyl, both for two cycles.

The test compositions of these examples were tested for their fungicidal activity by transferring each of four different amounts of each composition to a culture-containing Erlenmeyer flask. The amounts of test compositions (as shown in Table I below) were chosen so that 1X represented the manufacturers recommended field dosage, as a herbicide, for soybean crops. The four different amounts were 0.5×, 1×, 2×, and 4×. From each of the amended cultures then were transferred ten 10 ml aliquots, each aliquot to a 100 mm × 15 mm petri dish. A 2mm mycelial plug was transferred to each of the petri dishes, which were maintained at room temperature (about 25° C.) for 2 weeks. The fungus colony diameter was then measured and the colony area calculated for each petri dish media. The results are graphically illustrated in FIGS. 1 to 3 hereof.

To simulate repeat applications, or cycles, of test compositions, mycelial plugs from 4 week old cultures which had been treated with a test composition were transferred to fresh culture media containing the same test composition and treatment rate as the previous treatment. Media were prepared as previously mentioned and ten Petri dishes were poured for each treatment. This procedure was followed for each cycle. Colony area was again calculated after 2 weeks of fungal growth for each cycle with the results graphically illustrated in FIGS. 1 to 3 hereof.

TABLE I

| COMPOSITION | 1× | METRIC | VOL. % ACTIVE INGREDIENT | ACTIVE INGREDIENT (per petri dish/per hectare) .5× | 1× | 2× | 4× |
|---|---|---|---|---|---|---|---|
| ROUNDUP[1] | 16 oz/ACRE | 1.17 l/ha | 41% | 3.7 μl<br>.24 l | 7.4 μl<br>.48 l | 14.8 μl<br>.96 l | 29.6 μl<br>1.92 l |
| SCEPTER[2] | 14 oz/ACRE | 1.02 l/ha | 17.3% | 3.3 μl<br>.085 l | 6.6 μl<br>.17 l | 13.2 μl<br>.34 l | 26.4 μl<br>.68 l |
| CLASSIC[3] | 0.5 oz/ACRE | 35 g/ha | 25% | 10 μg<br>4.38 g | 20 μg<br>8.75 g | 40 μg<br>17.5 g | 80 μg<br>35 g |

[1]isopropylamine salt of N-phosphonomethyl glycine, commercially available under the tradename ROUNDUP and RODEO from Monsanto;
[2]2-[4,5-dihydro-4-methyl-4-(1-methylethyl)-5-oxo-1H-imidazol-2yl]-3-quinoline carboxylic acid, commercially available under the tradename SCEPTER from American Cyanamid and Co.;
[3]chlorimuron ethyl, commercially available under the tradename CLASSIC from American Cyanamid and Co.

The data represented in the Figures hereof evidence the unexpected fungicidal activity for the glyphosate and quinoline compositions, both of which are known commercial herbicides. Chlorimuron ethyl, also a known commercial herbicide did not exhibit the significant fungicidal activity toward the fungus Calonectria crotalariae.

Figure 3:
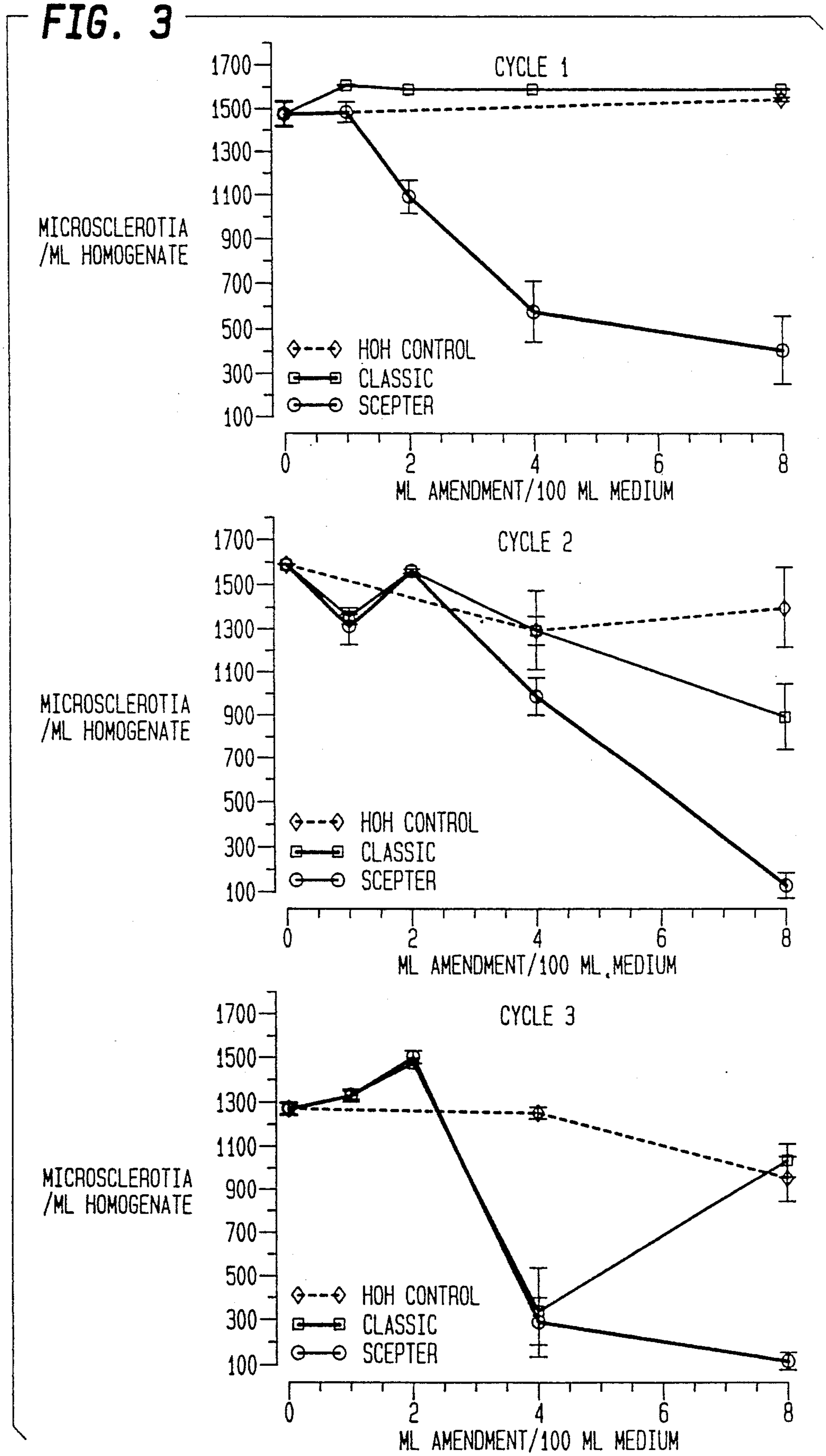
FIG. 3 is a plot of concentration of Calonectria crotalariae microsclerotia versus application rates for 2-[4,5-dihydro-4-methyl-4-(1-methylethyl)-5-oxo-1H-imidazol-2yl]-3-quinoline carboxylic acid and chlorimuron ethyl for three cycles.

These examples also include tests which were conducted as above except with a 50:50 mixture of ROUNDUP to SCEPTER. The fungal colony area results are graphically illustrated in FIG. 3 hereof. As can be seen in FIG. 3, a mixture of ROUNDUP and SCEPTER, at relatively low rates of each compound, is synergistically more effective as a fungicide against Calonectria crotalariae than each one alone. This is particularly unexpected because the synergistic effectiveness is observed even at treatment rates of ½ those recommended for the compositions as herbicides.

What is claimed is:

1. A method for protecting plants against soil-borne fungi, which method comprises: treating soil, which contains soil-borne fungi which are pathogenic to plants, with a fungicidally effective amount of a composition selected from the group consisting of : (a) 2-[4,5-dihydro-4-methyl-4-(1-methylethyl)-5-oxo-1H-imidazol-2-xy]-3-quinoline carboxylic acid mixed with agriculturally acceptable carriers: and (b) a mixture of isopropylamine salt of N-phosphonomethyl glycine, 2-[4,5-dihydro-4-methyl-4-(1-methylethyl)-5-oxo-1 -H-imidazol-2-yl]-2-quinoline carboxylic acid and agriculturally acceptable carriers.

2. The method of claim 1 wherein the ratio of isopropylamine salt of N-phosphonomethyl glycine to 2-[4,5-dihydro-4-methyl-4-(1-methylethyl)-5-oxo-1 H-imidazol-2-yl]-3-quinoline carboxylic acid in (b) is from 1:4 to 4:1.

3. The method of claim 2 wherein the ratio is 1:1.

* * * * *